United States Patent
Muri et al.

(10) Patent No.: US 11,065,153 B2
(45) Date of Patent: Jul. 20, 2021

(54) FLUIDICS CASSETTE FOR OCULAR SURGICAL SYSTEM

(71) Applicant: Johnson & Johnson Surgical Vision, Inc., Santa Ana, CA (US)

(72) Inventors: John I. Muri, Aliso Viejo, CA (US); Craig Edwards, Mission Viejo, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 350 days.

(21) Appl. No.: 14/815,914

(22) Filed: Jul. 31, 2015

(65) Prior Publication Data

US 2015/0335797 A1 Nov. 26, 2015

Related U.S. Application Data (62) Division of application No. 11/558,435, filed on Nov. 9, 2006, now Pat. No. 10,959,881.

(51) Int. Cl.
*A61F 9/007* (2006.01)
*A61M 1/00* (2006.01)

(52) U.S. Cl.
CPC ....... *A61F 9/00736* (2013.01); *A61M 1/0058* (2013.01); *A61M 2205/123* (2013.01);
(Continued)

(58) Field of Classification Search
CPC .... A61M 1/00; A61M 1/0007; A61M 1/0058; A61F 9/00736; A61F 9/00745
See application file for complete search history.

(56) References Cited

U.S. PATENT DOCUMENTS

| 1,848,024 A | 3/1932 | Owen |
| 2,123,781 A | 7/1938 | Huber |

(Continued)

FOREIGN PATENT DOCUMENTS

| AU | 2006235983 A1 | 5/2007 |
| CA | 2662797 A1 | 3/2008 |

(Continued)

OTHER PUBLICATIONS

International Search Report and Written Opinion for Application No. PCT/US2015/066036, dated Jul. 4, 2016, 20 pages.

(Continued)

*Primary Examiner* — Ariana Zimbouski
(74) *Attorney, Agent, or Firm* — Johnson & Johnson Surgical Vision, Inc.

(57) ABSTRACT

Methods, devices, and systems for laser eye surgery generally make use of a console that interchangeably accepts multiple types of eye treatment cassettes. The cassettes enable one or both of displacement-based or vacuum-based aspiration. The console and the cassette may communicate to establish the functionality of the installed cassette by utilizing a component indigenous to the operation of the cassette. A dual-mode cassette may include a separable holding tank for enabling vacuum-based aspiration. A displacement-based pump may be provided to drain the holding tank while the vacuum system continues to aspirate fluids. A vacuum sensor for controlling the flow of aspirated fluids may have three ports for communicating with a handpiece, a displacement-based pump, a vacuum-based pump, or an irrigation source. The handpiece may be vented during vacuum-based aspiration by opening a vent valve interposed between the handpiece and the vacuum source.

6 Claims, 9 Drawing Sheets

(52) U.S. Cl.
CPC ............... *A61M 2205/3569* (2013.01); *A61M 2205/505* (2013.01); *A61M 2205/6018* (2013.01); *A61M 2205/6036* (2013.01); *A61M 2210/0612* (2013.01)

(56) References Cited

U.S. PATENT DOCUMENTS

| | | | |
|---|---|---|---|
| 2,990,616 A | 7/1961 | Balamuth et al. | |
| 3,076,904 A | 2/1963 | Claus et al. | |
| 3,116,697 A | 1/1964 | Theodore | |
| 3,439,680 A | 4/1969 | Thomas, Jr. | |
| 3,526,219 A | 9/1970 | Lewis | |
| 3,781,142 A | 12/1973 | Zweig | |
| 3,857,387 A | 12/1974 | Shock | |
| 4,017,828 A | 4/1977 | Watanabe et al. | |
| 4,037,491 A | 7/1977 | Newbold | |
| 4,189,286 A | 2/1980 | Murry et al. | |
| 4,193,004 A | 3/1980 | Lobdell et al. | |
| 4,247,784 A | 1/1981 | Henry | |
| 4,276,023 A | 6/1981 | Phillips et al. | |
| 4,286,464 A | 9/1981 | Tauber et al. | |
| 4,479,760 A | 10/1984 | Bilstad et al. | |
| 4,537,561 A | 8/1985 | Xanthopoulos | |
| 4,564,342 A | 1/1986 | Weber et al. | |
| 4,590,934 A | 5/1986 | Malis et al. | |
| 4,662,829 A | 5/1987 | Nehring | |
| 4,665,621 A | 5/1987 | Ackerman et al. | |
| 4,706,687 A | 11/1987 | Rogers et al. | |
| 4,713,051 A | 12/1987 | Steppe et al. | |
| 4,757,814 A | 7/1988 | Wang et al. | |
| 4,758,220 A | 7/1988 | Sundblom et al. | |
| 4,758,238 A | 7/1988 | Sundblom et al. | |
| 4,772,263 A | 9/1988 | Dorman et al. | |
| 4,773,897 A | 9/1988 | Scheller et al. | |
| 4,818,186 A | 4/1989 | Pastrone et al. | |
| 4,819,317 A | 4/1989 | Bauer et al. | |
| 4,837,857 A | 6/1989 | Scheller et al. | |
| 4,920,336 A | 4/1990 | Meijer | |
| 4,920,645 A | 5/1990 | Baudouin | |
| 4,921,477 A | 5/1990 | Davis | |
| 4,925,444 A | 5/1990 | Orkin et al. | |
| 4,933,843 A | 6/1990 | Scheller et al. | |
| 4,941,518 A | 7/1990 | Williams et al. | |
| 4,954,960 A | 9/1990 | Lo et al. | |
| 4,961,424 A | 10/1990 | Kubota et al. | |
| 4,965,417 A | 10/1990 | Massie | |
| 4,983,901 A | 1/1991 | Lehmer | |
| 4,998,972 A | 3/1991 | Chin et al. | |
| 5,006,110 A | 4/1991 | Garrison et al. | |
| 5,020,535 A | 6/1991 | Parker et al. | |
| 5,026,387 A | 6/1991 | Thomas | |
| 5,032,939 A | 7/1991 | Mihara et al. | |
| 5,039,973 A | 8/1991 | Carballo | |
| 5,091,656 A | 2/1992 | Gahn | |
| 5,108,367 A | 4/1992 | Epstein et al. | |
| 5,110,270 A | 5/1992 | Morrick | |
| 5,125,891 A | 6/1992 | Hossain et al. | |
| 5,160,317 A | 11/1992 | Costin | |
| 5,195,960 A | 3/1993 | Hossain et al. | |
| 5,195,961 A | 3/1993 | Takahashi et al. | |
| 5,195,971 A | 3/1993 | Sirhan | |
| 5,230,614 A | 7/1993 | Zanger et al. | |
| 5,242,404 A | 9/1993 | Conley et al. | |
| 5,249,121 A | 9/1993 | Baum et al. | |
| 5,267,956 A * | 12/1993 | Beuchat | A61M 1/0058 604/153 |
| 5,268,624 A | 12/1993 | Zanger | |
| 5,271,379 A | 12/1993 | Phan et al. | |
| 5,282,787 A | 2/1994 | Wortrich | |
| 5,323,543 A | 6/1994 | Steen et al. | |
| 5,342,293 A | 8/1994 | Zanger | |
| 5,350,357 A | 9/1994 | Kamen et al. | |
| 5,351,676 A | 10/1994 | Putman | |
| 5,354,268 A | 10/1994 | Peterson et al. | |
| 5,364,144 A | 11/1994 | Satterfield et al. | |
| 5,378,126 A | 1/1995 | Abrahamson et al. |
| 5,388,569 A | 2/1995 | Kepley |
| 5,429,601 A | 7/1995 | Conley et al. |
| 5,445,506 A | 8/1995 | Afflerbaugh et al. |
| 5,454,783 A | 10/1995 | Grieshaber et al. |
| 5,464,391 A | 11/1995 | Devale |
| 5,470,211 A | 11/1995 | Knott et al. |
| 5,470,312 A | 11/1995 | Zanger et al. |
| 5,499,969 A | 3/1996 | Beuchat et al. |
| 5,505,330 A | 4/1996 | Nunes |
| 5,520,652 A | 5/1996 | Peterson |
| 5,533,976 A | 7/1996 | Zaleski et al. |
| 5,549,461 A | 8/1996 | Newland |
| 5,554,894 A | 9/1996 | Sepielli |
| 5,558,240 A | 9/1996 | Karp |
| 5,561,575 A | 10/1996 | Eways |
| 5,569,188 A | 10/1996 | Mackool |
| 5,580,347 A | 12/1996 | Reimels |
| 5,591,127 A | 1/1997 | Barwick et al. |
| 5,653,887 A | 8/1997 | Wahl et al. |
| 5,657,000 A | 8/1997 | Ellingboe |
| 5,676,530 A | 10/1997 | Nazarifar |
| 5,676,649 A | 10/1997 | Boukhny et al. |
| 5,676,650 A | 10/1997 | Grieshaber et al. |
| 5,693,020 A | 12/1997 | Rauh |
| 5,697,898 A | 12/1997 | Devine |
| 5,697,910 A | 12/1997 | Cole et al. |
| 5,700,240 A | 12/1997 | Barwick, Jr. et al. |
| 5,724,264 A | 3/1998 | Rosenberg et al. |
| 5,728,130 A | 3/1998 | Ishikawa et al. |
| 5,733,256 A | 3/1998 | Costin |
| 5,733,263 A | 3/1998 | Wheatman |
| 5,745,647 A | 4/1998 | Krause |
| 5,746,713 A | 5/1998 | Hood et al. |
| 5,747,824 A | 5/1998 | Jung et al. |
| 5,752,918 A | 5/1998 | Fowler et al. |
| 5,777,602 A | 7/1998 | Schaller et al. |
| 5,805,998 A | 9/1998 | Kodama |
| 5,807,075 A | 9/1998 | Jacobsen et al. |
| 5,810,765 A | 9/1998 | Oda |
| 5,810,766 A | 9/1998 | Barnitz et al. |
| 5,830,176 A | 11/1998 | Mackool |
| 5,843,109 A | 12/1998 | Mehta et al. |
| 5,859,642 A | 1/1999 | Jones |
| 5,871,492 A | 2/1999 | Sorensen |
| 5,879,298 A | 3/1999 | Drobnitzky et al. |
| 5,883,615 A | 3/1999 | Fago et al. |
| 5,899,674 A | 5/1999 | Jung et al. |
| 5,928,257 A | 7/1999 | Kablik et al. |
| 5,938,655 A | 8/1999 | Bisch et al. |
| 5,983,749 A | 11/1999 | Holtorf |
| 6,002,484 A | 12/1999 | Rozema et al. |
| 6,024,428 A | 2/2000 | Uchikata |
| 6,028,387 A | 2/2000 | Boukhny |
| 6,036,458 A | 3/2000 | Cole et al. |
| D423,349 S | 4/2000 | Lyons et al. |
| 6,062,829 A | 5/2000 | Ognier |
| 6,077,285 A | 6/2000 | Boukhny |
| 6,086,598 A | 7/2000 | Appelbaum et al. |
| 6,109,895 A | 8/2000 | Ray et al. |
| 6,117,126 A | 9/2000 | Appelbaum et al. |
| 6,139,320 A | 10/2000 | Hahn |
| 6,150,623 A | 11/2000 | Chen |
| 6,159,175 A | 12/2000 | Strukel et al. |
| 6,179,829 B1 | 1/2001 | Bisch et al. |
| 6,200,287 B1 | 3/2001 | Keller et al. |
| 6,219,032 B1 | 4/2001 | Rosenberg et al. |
| 6,251,113 B1 | 6/2001 | Appelbaum et al. |
| 6,260,434 B1 | 7/2001 | Holtorf |
| 6,360,630 B2 | 3/2002 | Holtorf |
| 6,368,269 B1 | 4/2002 | Lane |
| 6,383,804 B1 | 5/2002 | Ward, Jr. et al. |
| 6,411,062 B1 | 6/2002 | Baranowski et al. |
| 6,424,124 B2 | 7/2002 | Ichihara et al. |
| 6,436,072 B1 | 8/2002 | Kullas et al. |
| 6,452,120 B1 | 9/2002 | Chen |
| 6,452,123 B1 | 9/2002 | Chen |
| 6,491,661 B1 | 12/2002 | Boukhny et al. |
| 6,511,454 B1 | 1/2003 | Nakao et al. |

(56) References Cited

U.S. PATENT DOCUMENTS

| | | |
|---|---|---|
| 6,537,445 B2 | 3/2003 | Muller |
| 6,561,999 B1 | 5/2003 | Nazarifar et al. |
| 6,595,948 B2 | 7/2003 | Suzuki et al. |
| 6,632,214 B2 | 10/2003 | Morgan et al. |
| 6,674,030 B2 | 1/2004 | Chen et al. |
| 6,830,555 B2 | 12/2004 | Rockley et al. |
| 6,852,092 B2 | 2/2005 | Kadziauskas et al. |
| 6,862,951 B2 | 3/2005 | Peterson et al. |
| 6,908,451 B2 | 6/2005 | Brody et al. |
| 6,962,488 B2 | 11/2005 | Davis et al. |
| 6,962,581 B2 | 11/2005 | Thoe |
| 6,986,753 B2 | 1/2006 | Bui |
| 7,011,761 B2 | 3/2006 | Muller |
| 7,012,203 B2 | 3/2006 | Hanson et al. |
| 7,070,578 B2 | 7/2006 | Leukanech et al. |
| 7,073,083 B2 | 7/2006 | Litwin, Jr. et al. |
| 7,087,049 B2 | 8/2006 | Nowlin et al. |
| 7,103,344 B2 | 9/2006 | Menard |
| 7,167,723 B2 | 1/2007 | Zhang |
| 7,168,930 B2 | 1/2007 | Cull et al. |
| 7,169,123 B2 | 1/2007 | Kadziauskas et al. |
| 7,236,766 B2 | 6/2007 | Freeburg |
| 7,236,809 B2 | 6/2007 | Fischedick et al. |
| 7,242,765 B2 | 7/2007 | Hairston |
| 7,244,240 B2 | 7/2007 | Nazarifar et al. |
| 7,289,825 B2 | 10/2007 | Fors et al. |
| 7,300,264 B2 | 11/2007 | Souza |
| 7,316,664 B2 | 1/2008 | Kadziauskas et al. |
| 7,336,976 B2 | 2/2008 | Ito |
| 7,381,917 B2 | 6/2008 | Dacquay et al. |
| 7,439,463 B2 | 10/2008 | Brenner et al. |
| 7,465,285 B2 | 12/2008 | Hutchinson et al. |
| 7,470,277 B2 | 12/2008 | Finlay et al. |
| 7,526,038 B2 | 4/2009 | McNamara |
| 7,591,639 B2 | 9/2009 | Kent |
| 7,731,484 B2 | 6/2010 | Yamamoto et al. |
| 7,776,006 B2 | 8/2010 | Childers et al. |
| 7,785,316 B2 | 8/2010 | Claus et al. |
| 7,811,255 B2 | 10/2010 | Boukhny et al. |
| 7,883,521 B2 | 2/2011 | Rockley et al. |
| 7,921,017 B2 | 4/2011 | Claus et al. |
| 7,967,777 B2 | 6/2011 | Edwards et al. |
| 8,070,712 B2 | 12/2011 | Muri et al. |
| 8,075,468 B2 | 12/2011 | Min et al. |
| D693,463 S | 11/2013 | Burger et al. |
| D698,019 S | 1/2014 | Oliveira |
| 9,033,940 B2 | 5/2015 | Muri et al. |
| 9,658,468 B2 | 5/2017 | Dai |
| 2001/0023331 A1 | 9/2001 | Kanda et al. |
| 2001/0047166 A1 | 11/2001 | Wuchinich |
| 2001/0051788 A1 | 12/2001 | Paukovits et al. |
| 2002/0004657 A1 | 1/2002 | Morgan et al. |
| 2002/0007671 A1 | 1/2002 | Lavi et al. |
| 2002/0019215 A1 | 2/2002 | Romans |
| 2002/0045887 A1 | 4/2002 | Dehoogh et al. |
| 2002/0070840 A1 | 6/2002 | Fischer et al. |
| 2002/0098859 A1 | 7/2002 | Murata |
| 2002/0137007 A1 | 9/2002 | Beerstecher |
| 2002/0179462 A1 | 12/2002 | Silvers |
| 2002/0183693 A1 | 12/2002 | Peterson et al. |
| 2003/0028091 A1 | 2/2003 | Simon et al. |
| 2003/0050619 A1 | 3/2003 | Mooijman et al. |
| 2003/0083016 A1 | 5/2003 | Evans et al. |
| 2003/0108429 A1* | 6/2003 | Angelini ............ A61M 1/0066 417/3 |
| 2003/0125717 A1 | 7/2003 | Whitman |
| 2003/0224729 A1 | 12/2003 | Arnold |
| 2003/0226091 A1 | 12/2003 | Platenberg et al. |
| 2004/0019313 A1 | 1/2004 | Childers et al. |
| 2004/0037724 A1 | 2/2004 | Haser et al. |
| 2004/0097868 A1 | 5/2004 | Kadziauskas et al. |
| 2004/0127840 A1 | 7/2004 | Gara et al. |
| 2004/0193182 A1 | 9/2004 | Yaguchi et al. |
| 2004/0212344 A1 | 10/2004 | Tamura et al. |
| 2004/0215127 A1 | 10/2004 | Kadziauskas et al. |
| 2004/0224641 A1 | 11/2004 | Sinn |
| 2004/0253129 A1 | 12/2004 | Sorensen et al. |
| 2005/0039567 A1 | 2/2005 | Peterson et al. |
| 2005/0054971 A1 | 3/2005 | Steen et al. |
| 2005/0069419 A1 | 3/2005 | Cull et al. |
| 2005/0070859 A1 | 3/2005 | Cull et al. |
| 2005/0070871 A1 | 3/2005 | Lawton et al. |
| 2005/0095153 A1 | 5/2005 | Demers et al. |
| 2005/0103607 A1 | 5/2005 | Mezhinsky |
| 2005/0109595 A1 | 5/2005 | Mezhinsky et al. |
| 2005/0118048 A1* | 6/2005 | Traxinger ............ A61M 1/0058 417/477.2 |
| 2005/0119679 A1 | 6/2005 | Rabiner et al. |
| 2005/0130098 A1 | 6/2005 | Warner |
| 2005/0187513 A1 | 8/2005 | Rabiner et al. |
| 2005/0197131 A1 | 9/2005 | Ikegami |
| 2005/0209552 A1 | 9/2005 | Beck et al. |
| 2005/0228266 A1 | 10/2005 | McCombs |
| 2005/0236936 A1 | 10/2005 | Shiv et al. |
| 2005/0245888 A1* | 11/2005 | Cull .................... A61M 1/0001 604/317 |
| 2005/0261628 A1 | 11/2005 | Boukhny et al. |
| 2005/0267504 A1 | 12/2005 | Boukhny et al. |
| 2006/0035585 A1 | 2/2006 | Washiro |
| 2006/0036180 A1 | 2/2006 | Boukhny et al. |
| 2006/0041220 A1 | 2/2006 | Boukhny et al. |
| 2006/0046659 A1 | 3/2006 | Haartsen et al. |
| 2006/0074405 A1 | 4/2006 | Malackowski et al. |
| 2006/0078448 A1 | 4/2006 | Holden |
| 2006/0114175 A1 | 6/2006 | Boukhny |
| 2006/0145540 A1 | 7/2006 | Mezhinsky |
| 2006/0219049 A1 | 10/2006 | Horvath et al. |
| 2006/0219962 A1 | 10/2006 | Dancs et al. |
| 2006/0224107 A1 | 10/2006 | Claus et al. |
| 2006/0236242 A1 | 10/2006 | Boukhny et al. |
| 2007/0016174 A1 | 1/2007 | Millman et al. |
| 2007/0049898 A1 | 3/2007 | Hopkins et al. |
| 2007/0060926 A1 | 3/2007 | Escaf |
| 2007/0073214 A1 | 3/2007 | Dacquay et al. |
| 2007/0073309 A1 | 3/2007 | Kadziauskas et al. |
| 2007/0078379 A1 | 4/2007 | Boukhny et al. |
| 2007/0085611 A1 | 4/2007 | Gerry et al. |
| 2007/0107490 A1 | 5/2007 | Artsyukhovich et al. |
| 2007/0231205 A1 | 10/2007 | Williams et al. |
| 2007/0248477 A1 | 10/2007 | Nazarifar et al. |
| 2007/0249942 A1 | 10/2007 | Salehi et al. |
| 2007/0252395 A1 | 11/2007 | Williams et al. |
| 2007/0287959 A1 | 12/2007 | Walter et al. |
| 2008/0033342 A1 | 2/2008 | Staggs |
| 2008/0066542 A1 | 3/2008 | Gao |
| 2008/0082040 A1 | 4/2008 | Kubler et al. |
| 2008/0112828 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1 | 5/2008 | Muri et al. |
| 2008/0114312 A1 | 5/2008 | Muri et al. |
| 2008/0114387 A1 | 5/2008 | Hertweck et al. |
| 2008/0125694 A1 | 5/2008 | Domash |
| 2008/0125695 A1 | 5/2008 | Hopkins et al. |
| 2008/0125697 A1 | 5/2008 | Gao |
| 2008/0125698 A1 | 5/2008 | Gerg et al. |
| 2008/0129695 A1 | 6/2008 | Li |
| 2008/0146989 A1 | 6/2008 | Zacharias |
| 2008/0200878 A1 | 8/2008 | Davis et al. |
| 2008/0243105 A1 | 10/2008 | Horvath |
| 2008/0262476 A1 | 10/2008 | Krause et al. |
| 2008/0281253 A1 | 11/2008 | Injev et al. |
| 2008/0294087 A1 | 11/2008 | Steen et al. |
| 2008/0312594 A1 | 12/2008 | Urich et al. |
| 2009/0005712 A1 | 1/2009 | Raney |
| 2009/0005789 A1 | 1/2009 | Charles |
| 2009/0048607 A1 | 2/2009 | Rockley |
| 2009/0087327 A1 | 4/2009 | Voltenburg, Jr. et al. |
| 2009/0124974 A1 | 5/2009 | Crank et al. |
| 2009/0163853 A1 | 6/2009 | Cull et al. |
| 2010/0036256 A1 | 2/2010 | Boukhny et al. |
| 2010/0057016 A1 | 3/2010 | Dale et al. |
| 2010/0069825 A1 | 3/2010 | Raney |

(56) References Cited

U.S. PATENT DOCUMENTS

| | | |
|---|---|---|
| 2010/0069828 A1 | 3/2010 | Steen et al. |
| 2010/0140149 A1 | 6/2010 | Fulkerson et al. |
| 2010/0152685 A1 | 6/2010 | Goh |
| 2010/0185150 A1 | 7/2010 | Zacharias |
| 2010/0249693 A1 | 9/2010 | Links |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0092962 A1 | 4/2011 | Ma et al. |
| 2011/0098721 A1 | 4/2011 | Tran et al. |
| 2011/0160646 A1 | 6/2011 | Kadziauskas et al. |
| 2011/0208047 A1 | 8/2011 | Fago |
| 2011/0251569 A1 | 10/2011 | Turner et al. |
| 2011/0300010 A1 | 12/2011 | Jarnagin et al. |
| 2012/0065580 A1 | 3/2012 | Gerg et al. |
| 2012/0078181 A1 | 3/2012 | Smith et al. |
| 2012/0083735 A1 | 4/2012 | Pfouts |
| 2012/0083736 A1 | 4/2012 | Pfouts et al. |
| 2012/0083800 A1 | 4/2012 | Andersohn |
| 2013/0072853 A1 | 3/2013 | Wong et al. |
| 2013/0169412 A1 | 7/2013 | Roth |
| 2013/0184638 A1 | 7/2013 | Scarpaci et al. |
| 2013/0184676 A1 | 7/2013 | Kamen et al. |
| 2013/0245543 A1 | 9/2013 | Gerg et al. |
| 2013/0267892 A1 | 10/2013 | Woolford et al. |
| 2013/0289475 A1 | 10/2013 | Muri et al. |
| 2013/0303978 A1 | 11/2013 | Ross |
| 2013/0336814 A1 | 12/2013 | Kamen et al. |
| 2014/0178215 A1 | 6/2014 | Baxter et al. |
| 2014/0188076 A1 | 7/2014 | Kamen et al. |
| 2014/0276424 A1 | 9/2014 | Davis et al. |
| 2016/0151564 A1 | 6/2016 | Magers et al. |

FOREIGN PATENT DOCUMENTS

| | | |
|---|---|---|
| DE | 3826414 A1 | 2/1989 |
| EP | 56019 A1 | 7/1982 |
| EP | 424687 A1 | 5/1991 |
| EP | 619993 A1 | 10/1994 |
| EP | 1010437 A1 | 6/2000 |
| EP | 1072285 A1 | 1/2001 |
| EP | 1113562 A1 | 7/2001 |
| EP | 1464310 A1 | 10/2004 |
| EP | 1469440 A2 | 10/2004 |
| EP | 1550406 A2 | 7/2005 |
| EP | 1704839 A1 | 9/2006 |
| EP | 1779879 A1 | 5/2007 |
| EP | 1787606 A1 | 5/2007 |
| EP | 1849443 A1 | 10/2007 |
| EP | 1849444 A1 | 10/2007 |
| EP | 1857128 A1 | 11/2007 |
| EP | 1310267 B1 | 1/2008 |
| EP | 1873501 A1 | 1/2008 |
| EP | 1900347 A1 | 3/2008 |
| EP | 1925274 A2 | 5/2008 |
| EP | 1867349 B1 | 11/2008 |
| ES | 2264369 A1 | 12/2006 |
| GB | 2230301 A | 10/1990 |
| GB | 2352887 A | 2/2001 |
| GB | 2438679 A | 12/2007 |
| JP | S5724482 A | 2/1982 |
| JP | S58167333 A | 10/1983 |
| JP | S62204463 A | 9/1987 |
| JP | 2005195653 A | 7/2005 |
| JP | 2008188110 A | 8/2008 |
| WO | 9220310 A1 | 11/1992 |
| WO | 9315777 A2 | 8/1993 |
| WO | 9317729 A1 | 9/1993 |
| WO | 9324082 A1 | 12/1993 |
| WO | 9405346 A1 | 3/1994 |
| WO | 9632144 A1 | 10/1996 |
| WO | 9737700 A1 | 10/1997 |
| WO | 9818507 A1 | 5/1998 |
| WO | 9917818 A1 | 4/1999 |
| WO | 0000096 A1 | 1/2000 |
| WO | 0070225 A1 | 11/2000 |
| WO | 0122696 A1 | 3/2001 |
| WO | 0226286 A2 | 4/2002 |
| WO | 0228449 A2 | 4/2002 |
| WO | 0234314 A1 | 5/2002 |
| WO | 03102878 A1 | 12/2003 |
| WO | 04096360 A1 | 11/2004 |
| WO | 2004114180 A1 | 12/2004 |
| WO | 05084728 A2 | 9/2005 |
| WO | 05092023 A2 | 10/2005 |
| WO | 05092047 A2 | 10/2005 |
| WO | 06101908 A2 | 9/2006 |
| WO | 06125280 A1 | 11/2006 |
| WO | 2007121144 A1 | 10/2007 |
| WO | 2007143677 A2 | 12/2007 |
| WO | 2007143797 A1 | 12/2007 |
| WO | 2007149637 A2 | 12/2007 |
| WO | 2008030872 A1 | 3/2008 |
| WO | 2008060859 A1 | 5/2008 |
| WO | 2008060902 A1 | 5/2008 |
| WO | 2008060995 A1 | 5/2008 |
| WO | 2009123547 A1 | 10/2009 |
| WO | 2010054146 A1 | 5/2010 |
| WO | 2010054225 A2 | 5/2010 |
| WO | 2010151704 A1 | 12/2010 |
| WO | 2012151062 A1 | 11/2012 |
| WO | 2013142009 A1 | 9/2013 |
| WO | 2015009945 A1 | 1/2015 |

OTHER PUBLICATIONS

International Search Report and Written Opinion for Application No. PCT/US2016/061648, dated Feb. 7, 2017, 12 pages.

"At Issue: venturi vs. peristaltic pumps," Ocular Surgery News U.S. Edition, Sep. 1, 2003, 6 pages.

Boyd, "Preparing for the Transition" in: The Art and the Science of Cataract Surgery, Chapter 7, 2001, pp. 93-133.

Definition of "Parameter", Retrieved from the Internet:.

English Human Translation of JP57024482 from Feb. 9, 1982.

European Search Report for Application No. EP10164058, dated Jun. 25, 2010, 2 pages.

European Search Report for Application No. EP13184138.9, dated Oct. 24, 2013, 7 pages.

Examination Report dated Mar. 28, 2012 for European Application No. EP09791072 filed Jul. 31, 2009, 3 pages.

Merritt R., et al., Wireless Nets Starting to link Medical Gear [online] 2004 [retrieved on Feb. 12, 2007]. Retrieved from the Internet:.

Phacoemulsification, [online] [retrieved on Jul. 1, 2009]. Retrieved from the Internet: , 2 pages.

International Search Report and Written Opinion for Application No. PCT/US2016/049970, dated Dec. 5, 2016, 12 pages.

"4.2.1 Design/Operating principle," Pfeiffer Vacuum, Retrieved from the Internet: (https://www.pfeiffer-vacuum.com/en/know-how/vacuum-generation/rotar-vane-vauum-pumps/design-operating-principle/), printed Oct. 31, 2020.

"An Introduction to Rotary Vane Vacuum Pumps," Gardner Denver GmbH, Retrieved from the Internet:: (https://www.gardnerdenver.com/en-us/knowledge-hub/articles/an-introduction-to-rotary-vane-vacuum-pumps), printed Oct. 31, 2020.

"Rotary Vane Vacuum Pumps," Becker Pumps Corporation, Retrieved from the Internet:: (https://beckerpumps.com/rotary-vane-oil-less-vacuum-pumps/), printed Oct. 31, 2020.

\* cited by examiner

FLUIDICS CASSETTE FOR OCULAR SURGICAL SYSTEM

CROSS-REFERENCED TO RELATED APPLICATIONS

This application claims priority to and is a divisional application of U.S. Nonprovisional application Ser. No. 11/558,435 filed on Nov. 9, 2006, the entire contents of which are incorporated herein by reference.

BACKGROUND OF THE INVENTION

The present invention is generally related to methods, devices, and systems for controlling surgical fluid flows, particularly during treatment of an eye.

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil, and within a capsular bag. This capsular bag is a thin, relatively delicate structure which separates the eye into anterior and posterior chambers.

With age, clouding of the lens or cataracts are fairly common. Cataracts may form in the hard central nucleus of the lens, in the softer peripheral cortical portion of the lens, or at the back of the lens near the capsular bag.

Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens, and maintains the separation between the anterior portion of the eye and the vitreous humour in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms have been used in phacoemulsification and other treatment systems for the eyes, aspiration flow systems can generally be classified in two categories: 1) volumetric-based aspiration flow systems using positive displacement pumps; and 2) vacuum-based aspiration systems using a vacuum source, typically applied to the aspiration flow through an air-liquid interface. These two categories of aspiration flow systems each have unique characteristics that render one more suitable for some procedures than the other, and vice versa.

Among positive displacement aspiration systems, peristaltic pumps (which use rotating rollers that press against a flexible tubing to induce flow) are commonly employed. Such pumps provide accurate control over the flow volume. The pressure of the flow, however, is less accurately controlled and the variations in vacuum may result in the feel or traction of the handpiece varying during a procedure. Peristaltic and other displacement pump systems may also be somewhat slow.

Vacuum-based aspiration systems provide accurate control over the fluid pressure within the eye, particularly when combined with gravity-fed irrigation systems. While vacuum-based systems can result in excessive fluid flows in some circumstances, they provide advantages, for example, when removing a relatively large quantity of the viscous vitreous humour from the posterior chamber of the eye. However, vacuum-based aspiration flow systems connected to Venturi pumps, rotary vane pumps, and other vacuum sources are subject to pressure surges during occlusion of the treatment probe, and such pressure surges may decrease the surgeon's control over the eye treatment procedure.

Different tissues may be aspirated from the anterior chamber of the eye with the two different types of aspiration flow. For example, vacuum-induced aspiration flow may quickly aspirate tissues at a significant distance from a delicate structure of the eye (such as the capsular bag), while tissues that are closer to the capsular bag are aspirated more methodically using displacement-induced flows.

Conventionally, fluid aspiration systems include a console and a fluidic cassette mounted on the console. The fluidic cassette is changed for each patient and cooperates with the console to provide fluid aspiration. Generally, a single type of cassette is used by a particular console, regardless of whether the procedure will require positive displacement aspiration, vacuum-based aspiration, or both.

In light of the above, it would be advantageous to provide improved devices, systems, and methods for eye surgery.

It would be particularly advantageous if these improvements allowed a console to interchangeably accept different types of cassettes tailored to the type of procedure to be performed.

It would also be particularly advantageous if the console and the cassette automatically communicated to establish the functionalities of the mounted cassette.

It would also be particularly advantageous if the different types of cassettes were modularly produced using common components.

It would also be particularly advantageous if improved means are provided for controlling the volume of the irrigation flow.

BRIEF SUMMARY OF THE INVENTION

The present invention is generally directed to improved methods, devices, and systems for eye surgery. In some embodiments, the invention may provide a console that interchangeably accepts multiple types of fluidic cassettes. The multiple types of cassettes may enable one or both of displacement-based and vacuum-based eye surgery fluid management systems during phacoemulsification, vitreotomy, therapies of the retina, and other treatments that involve penetration into one or more chambers of the eye. The console and the cassettes may automatically communicate to establish the available aspiration modes of the mounted cassette and activate the appropriate mechanisms to enable functionality of the cassettes. Establishment of an available mode or functionality of the cassettes may be passively provided so that a component and/or function indigenous to the operation of one of the cassettes, but not another, is utilized to provide the mode or functionality of one or both cassettes.

Optionally, both displacement and vacuum pumping components may be included in a first type of cassette, and only positive displacement components may be provided in a second type of cassette. Multiple types of fluidic cassettes may be fabricated using a common frame and have visual indicia that identify the type of cassette to a system user. The multiple types of fluidic cassettes may be interchangeably accepted by the console and may include functional indicators that identify to the console the functionalities of the cassettes. A dual mode cassette that enables both displacement-based and vacuum-based fluid aspiration may provide a further displacement-based pump for draining the holding tank of the vacuum-based aspiration system while the vacuum system continues operation. The dual mode cassette may include an additional, separably coupled holding tank and may provide venting via a vent valve interposed between the holding tank and the vacuum source. A vacuum sensor may also be provided having three ports for connection to the handpiece, a displacement-based pump, and, alternatively, a vacuum source or an irrigation source.

One aspect of the present invention is directed to an eye treatment system that includes an eye treatment probe, a console having a cassette receptacle, and a cassette received in the receptacle configured to couple the console with the probe. The console and the received cassette may communicate to establish a functionality of the cassette. In related aspects, the console may detects a functional indicator of the received cassette. The functional indicator may comprise an indigenous component of the cassette and/or console, for example, a connecting stem an indigenous holding tank actuates a microswitch or optical switch within the console. The functionality of the cassette may comprise displacement-based aspiration induced by a peristaltic pump formed by engagement of the cassette with the console. The functionality of the cassette may comprise vacuum-based aspiration induced by a Venturi or rotary vane pump in the console.

Another aspect of the present invention is directed to a method for operating a surgical console with an eye treatment cassette. The eye treatment cassette is received in a cassette receptacle of the console. The console and the cassette communicate to establish a functionality of the cassette. Vacuum-based aspiration is enabled when the functionality is detected in the cassette.

Another aspect of the present invention is directed to eye treatment cassettes of multiple types configured to interchangeably couple with the same surgical console. A first type of cassette enables displacement-based aspiration when coupled with the console and a second type of cassette enables both displacement-based aspiration and vacuum-based aspiration when coupled with the console. The second type of cassette comprises a separably coupled holding tank for enabling the vacuum-based aspiration. In related aspects, the second type of cassette may comprise the holding tank separably coupled to a fluid network of the first type of cassette. The holding tank may connect to a vacuum source in the console and to a collection bag. The holding tank may communicate to the console that vacuum-based aspiration is available when the second type of cassette is coupled with the console.

Another aspect of the present invention is directed to a method for manufacturing eye treatment cassettes of multiple types configured to interchangeably couple with the same surgical console. A first type of cassette having a fluid network is made for enabling displacement-based aspiration when coupled with the console. A second type of cassette is made for enabling both displacement-based aspiration and vacuum-based aspiration when coupled with the console by separably coupling a holding tank to the fluid network used for the first type of cassette.

Another aspect of the present invention is directed to an eye treatment cassette that includes a fluid network for aspirating fluids from an eye of a patient, and a vacuum sensor connected to the fluid network for controlling a flow of the aspirated fluids having a first port for connecting to a handpiece and second and third ports. In related aspects, the second port connects to a displacement-based pump and the third port alternatively connects to a vacuum source or an irrigation source.

Another aspect of the present invention is directed to a method for venting a handpiece of an eye treatment cassette. The eye treatment cassette is operated such that a vacuum is induced at the handpiece by a vacuum source communicating with the handpiece. The handpiece is vented by opening a vent valve interposed between the vacuum source and the handpiece.

Another aspect of the present invention is directed to an eye treatment cassette that includes a handpiece configured to aspirate fluids from a patient's eye, a vacuum source communicating with the handpiece, and a vent valve interposed between the vacuum source and the handpiece configured to vent the handpiece when opened.

Another aspect of the present invention is directed to a method for draining aspirated fluids collected in a holding tank of an eye treatment cassette. A vacuum source connected to a handpiece via the holding tank continues to operate while a displacement-based pump connected between the holding tank and a collection bag operates to drain the aspirated fluids into the collection bag.

Another aspect of the present invention is directed to an eye treatment cassette that includes a handpiece configured to aspirate fluids from a patient's eye, a vacuum source communicating with the handpiece, a holding tank interposed between the handpiece and the vacuum source configured to hold the aspirated fluids, and a collection bag connected to the holding tank for collecting the aspirated fluids. A displacement-based pump interposed between the holding tank and the collection bag is configured to operate while the vacuum source continues to aspirate fluids via the handpiece to drain the aspirated fluids into the collection bag.

DETAILED DESCRIPTION OF THE INVENTION

The present invention generally provides improved devices, systems, and methods for treating an eye of the patient.

In one embodiment of the present invention, a fluid aspiration system includes a console on which multiple types of interchangeable fluidic cassettes can be mounted. Each type of cassette may include components for enabling one or both of displacement-based and vacuum-based aspiration. The cassette may include a surgical fluid network, and mounting of the cassette to the console allows various network elements of the cassette to interface with corresponding components of the console. The fluid network of the cassette may include resiliently deformable tubing, a pressure sensor, a holding tank or chamber, and the like. The components of the fluid network may change depending on whether the cassette enables displacement-based or vacuum-based aspiration, or both. For example, in order to enable displacement-based aspiration, a cassette body may constrain a segment of the tubing in an arcuate configuration, so that when the cassette is mounted to the console, a peristaltic drive rotor of the console engages the arc segment of tubing. This allows positive displacement pumping of aspiration fluid from the eye, through the probe, and into a waste receptacle. When vacuum-based aspiration is needed, the fluid network of the cassette may include a vacuum chamber drawing on a vacuum source within the console.

Figure 1:
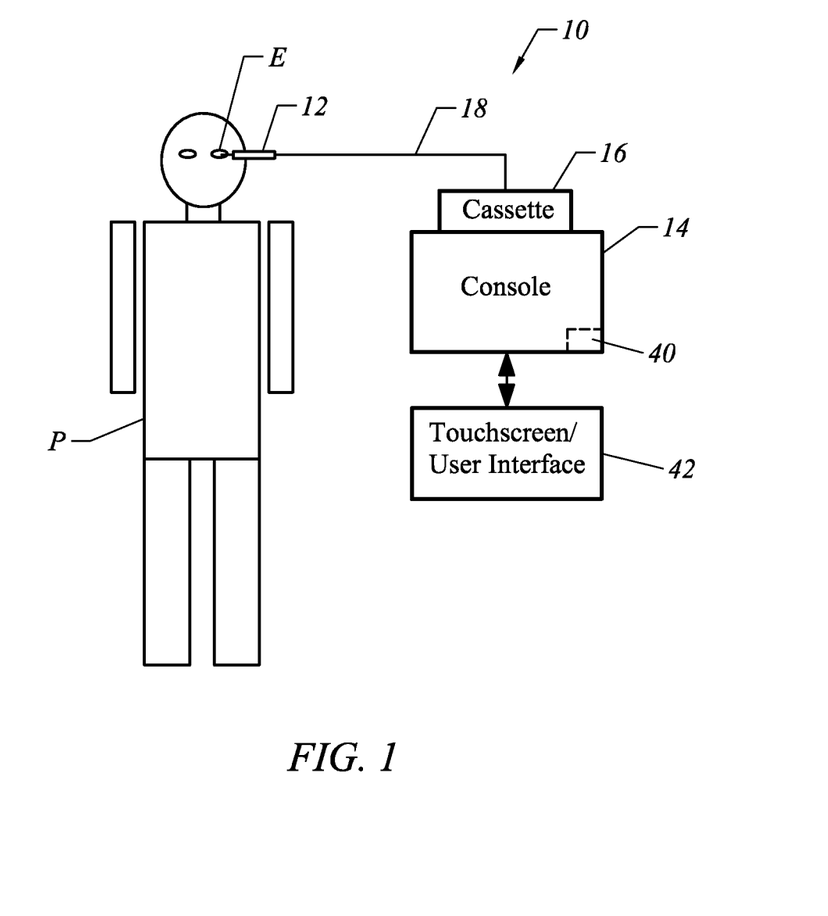
FIG. 1 schematically illustrates an eye treatment system in which a cassette couples an eye treatment probe with an eye treatment console, along with a method for use of the system for treating the eye of a patient.

Referring to FIG. 1, a system 10 for treating an eye E of a patient P generally includes an eye treatment probe handpiece 12 coupled to a console 14 by a cassette 16 mounted on the console. Handpiece 12 generally includes a handle for manually manipulating and supporting an insertable probe tip. The probe tip has a distal end which is insertable into the eye, with one or more lumens in the probe tip allowing irrigation fluid to flow from the console 14 and/or cassette 16 into the eye. Aspiration fluid may also be withdrawn through a lumen of the probe tip, with the console 14 and cassette 16 generally including a vacuum aspiration source, a positive displacement aspiration pump, or both to help withdraw and control a flow of surgical fluids into and out of eye E. As the surgical fluids may include biological materials that should not be transferred between patients, cassette 16 will often comprise a disposable (or alternatively, sterilizable) structure, with the surgical fluids being transmitted through flexible conduits 18 of the cassette that avoid direct contact in between those fluids and the components of console 14.

When a distal end of the probe tip of handpiece 12 is inserted into an eye E (for example) for removal of a lens of a patient with cataracts, an electrical conductor (not shown) may supply energy from console 14 to an ultrasound transmitter of the handpiece. Alternatively, the handpiece 12 may be configured as an I/A or vitrectomy handpiece. Also, the ultrasonic transmitter may be replaced by other means for emulsifying a lens, such as a high energy laser beam. The ultrasound energy from handpiece 12 helps to fragment the tissue of the lens, which can then be drawn into a port of the tip by aspiration flow. So as to balance the volume of material removed by the aspiration flow, an irrigation flow through handpiece 12 (or a separate probe structure) may also be provided, with both the aspiration and irrigations flows being controlled by console 14.

So as to avoid cross-contamination between patients without incurring excessive expenditures for each procedure, cassette 16 and its flexible conduit 18 may be disposable. Alternatively, the flexible conduit or tubing may be disposable, with the cassette body and/or other structures of the cassette being sterilizable. Regardless, the disposable components of the cassette are typically configured for use with a single patient, and may not be suitable for sterilization. The cassette will interface with reusable (and often quite expensive) components of console 14, including peristaltic pump rollers, a Venturi pump, rotary vane pump, or other vacuum source, a controller 40, and the like.

Controller 40 may include an embedded microcontroller and/or many of the components of a personal computer, such as a processor, a data bus, a memory, input and/or output devices (including a touch screen user interface 42), and the like. Controller 40 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 40 may have (or be coupled to) a recording media reader, or the code may be transmitted to controller 40 by a network connection such as an internet, an intranet, an Ethernet™, a wireless network, or the like. Along with programming code, controller 40 may include stored data for implementing the methods described herein, and may generate and/or store data that records perimeters with corresponding to the treatment of one or more patients. Many components of console 14 may be found in or modified from known commercial phacoemulsification systems from Advanced Medical Optics Inc. of Santa Ana, Calif.; Alcon Manufacturing, Ltd. of Ft. Worth, Tex., Bausch and Lomb of Rochester, N.Y., and other suppliers.

Figures 2, 3:
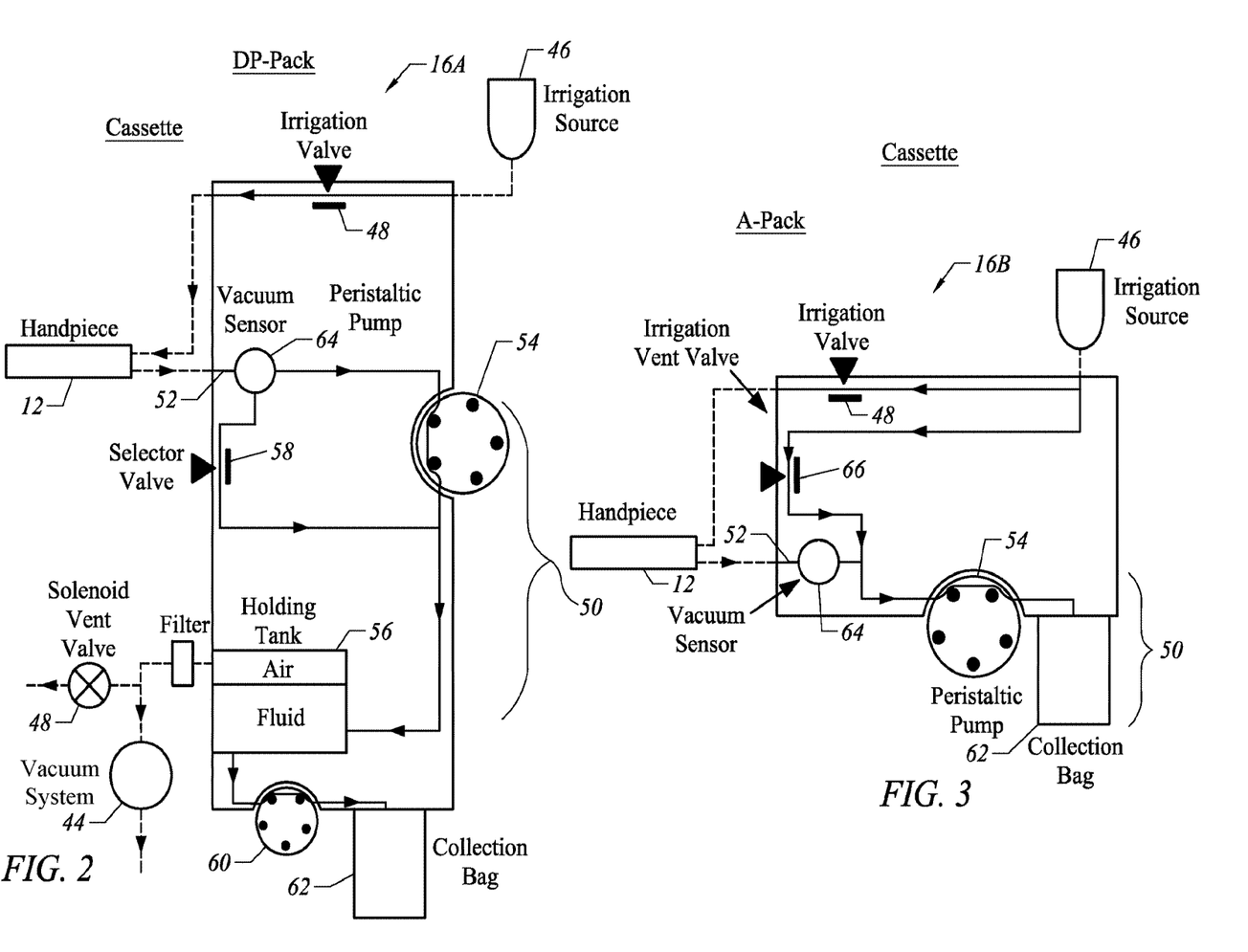
FIG. 2 schematically illustrates a dual mode cassette having a surgical fluid pathway network for use in the system of FIG. 1.
FIG. 3 schematically illustrates a single mode displacement-based aspiration cassette having a surgical fluid pathway network for use in the system of FIG. 1.

Referring now to FIGS. 1 and 2, components of the aspiration and irrigation fluid flow networks of system 10 are described in more detail with respect to a dual mode cassette 16A that enables both displacement-based and/or vacuum-based aspiration modes. FIG. 2 generally highlights the surgical aspiration and irrigation fluid control elements included within the cassette 16A, with the irrigation components often being relatively straightforward. An irrigation source 46 of, and/or controlled by, the console optionally provides irrigation fluid pressure control via an irrigation line 51 by relying at least in part on a gravity pressure head that varies with a height of an irrigation fluid bag or the like. An irrigation on/off pinch valve 48 may generally include a short segment of a flexible conduit of cassette 16A, which can be engaged and actuated by an actuator of the console 14, with a surface of the cassette body often being disposed opposite the actuator to facilitate closure of the conduit lumen. Alternative irrigation flow systems may include positive displacement pumps, alternative fluid pressurization drive systems, fluid pressure or flow modulating valves, and/or the like. In certain embodiments, irrigation fluid is alternatively or additionally provided to a separate handpiece (not shown).

The aspiration flow network 50 generally provides an aspiration flow path 52 that can couple an aspiration port in the tip of handpiece 12 to either a peristaltic pump 54, formed by engagement of the cassette with the console, and/or a holding tank 56. Fluid aspirated through the handpiece 12 may be contained in holding tank 56 regardless of whether the aspiration flow is induced by peristaltic pump 54 or the vacuum applied to the holding tank 56. When valve 58 is closed and peristaltic pump 54 is in operation, pumping of the aspiration flow may generally be directed by the peristaltic pump 54, independent of the pressure in the holding tank 56. Conversely, when peristaltic pump 54 is off, flow through the peristaltic pump may be halted by pinching of the elastomeric tubing arc of the peristaltic pump by one or more of the individual rollers of the peristaltic pump rotor. Hence, any aspiration fluid drawn into the aspiration network when peristaltic pump 54 is off will typically be effected by opening of a selector control valve 58 so that the aspiration port of the probe is in fluid communication with the holding tank. Regardless, the pressure within tank 56 may be maintained at a controlled vacuum level, often at a fixed vacuum level, by a vacuum system 44 of the console. The vacuum system 44 may comprise a Venturi pump, a rotary vane pump, a vacuum source, or the like. Aspiration flow fluid that drains into holding tank 56 may be removed by a peristaltic drain pump 60 and directed to a disposal fluid collection bag 62. Vacuum pressure at the surgical handpiece may be maintained within a desired range through control of the fluid level in the holding tank. In particular, peristaltic drain pump 60 enables the holding tank 56 to be drained while vacuum-based aspiration continues using vacuum system 44.

In more detail, the operation of aspiration flow network 50 can be understood by first considering the flow when valve 58 is closed. In this mode, peristaltic pump 54 draws fluid directly from handpiece 12, with a positive displacement peristaltic pump flow rate being controlled by the system controller 40 (see FIG. 1). To determine the appropriate flow rate, the level of vacuum within the aspiration flow network may be identified in part with reference to a vacuum sensor 64 with three ports disposed along the aspiration flow network 50 between peristaltic pump 54, handpiece 12, and selector valve 58. This allows the system to detect and adjust for temporary occlusions of the handpiece and the like. Venting or reflux of the handpiece 12 in this state may be achieved by reversing the rotation of peristaltic pump 54 or by opening selector valve 58 to equalize fluid pressures. Selector valve 58 may be configured as a variable restrictor to regulate the amount of fluid that is vented from the high pressure side of peristaltic pump 54 to the low pressure side. In this mode, while the aspiration material flows through holding tank 56 and eventually into collection bag 62, the holding tank pressure may have little or no effect on the flow rate.

When peristaltic pump 54 is not in operation, rotation of the peristaltic pump is may be inhibited and the rotors of the peristaltic pump generally pinch the arcuate resilient tubing of the probe so as to block aspiration flow. Material may then be drawn into the aspiration port of handpiece 12 by opening selector valve 58 and engagement or operation of the vacuum system 44. When valve 58 is open, the aspiration port draws fluid therein based on the pressure differential between holding tank 56 and the chamber of the eye in which the fluid port is disposed, with the pressure differential being reduced by the total pressure loss of the aspiration flow along the aspiration path between the tank and port. In this mode, venting or reflux of the handpiece 12 may be accomplished by opening the solenoid vent valve 48', which pressurizes the holding tank 56 to increase the tank pressure and push fluid back towards (i.e., "vents") the handpiece 12. In some embodiments, the vent valve 48' may be used to increase the pressure inside the tank 56 to at or near atmospheric pressure. Alternatively, venting of the handpiece may be accomplished in this mode by closing selector valve 58, and by rotation peristaltic pump 54 in reverse (e.g., clockwise in FIG. 2). Accordingly, aspiration network 50 of the dual mode cassette 16A allows system 10 to operate in either peristaltic or vacuum-based pumping modes and to incorporate three different venting modes. In some embodiments, an additional valve is added to the cassette 16A that may be used to fluidly couple the irrigation line 51 to the aspiration flow network 50, thus providing an addition option for venting or refluxing the handpiece 12.

When only displacement-based pumping will be used for a particular procedure, an alternative cassette may be employed in the console 14, with the alternative cassette lacking a holding tank 56, selector valve 58, and the like. Referring now to FIGS. 1 and 3, components of a single mode cassette 16B are described, the single mode cassette enabling only the displacement-based aspiration mode. Within the single mode cassette, peristaltic pump 54 draws fluid directly from handpiece 12, with a positive displacement peristaltic pump flow rate being controlled by the system controller 40 (see FIG. 1). To determine the appropriate flow rate, the level of vacuum within the aspiration flow network may be identified in part with reference to a vacuum sensor 64 with three ports disposed along the aspiration flow network 50 between peristaltic pump 54, handpiece 12, and irrigation vent valve 66. The aspiration material flows directly into collection bag 62. Alternatively, a single mode cassette may also be provided that only enables vacuum-based aspiration.

As a dual mode cassette may be somewhat more complex, a single mode cassette may be both simpler and less expensive. Therefore, the present invention may avoid complexity and provide cost savings by enabling the use of a less expensive single mode cassette when only a single aspiration mode is needed during a procedure on a particular patient.

Figure 4:
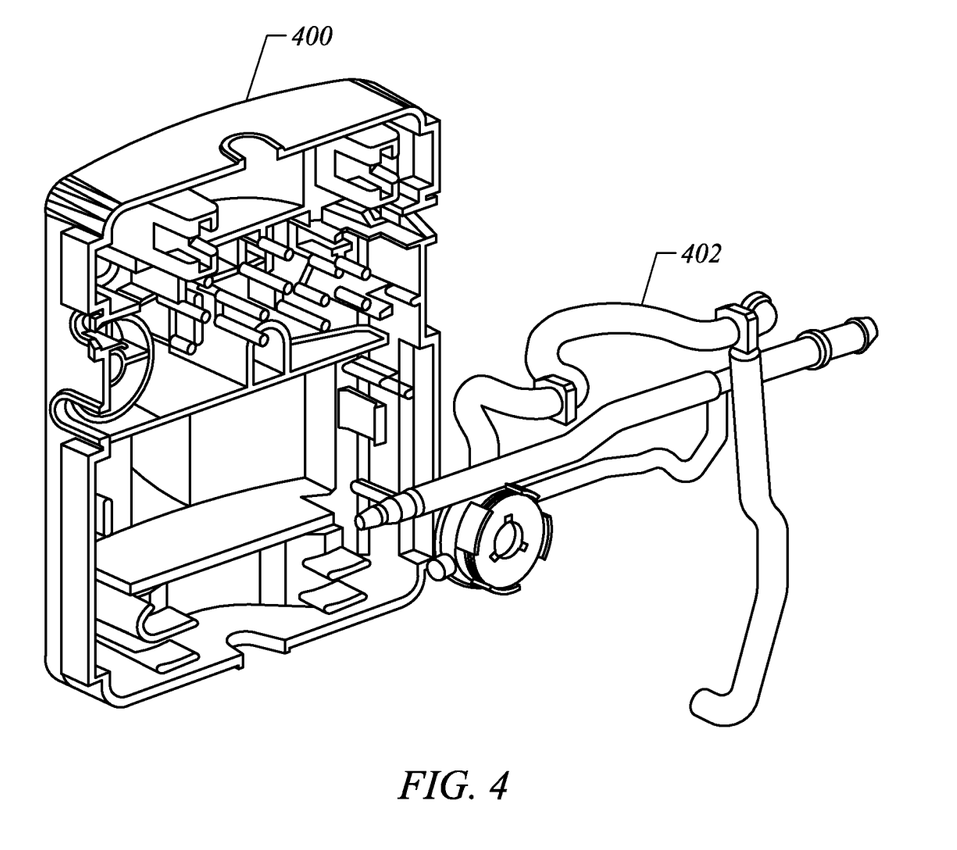
FIG. 4 is a perspective view showing a single mode fluid network that is mountable on a common cassette frame.
Figure 5:
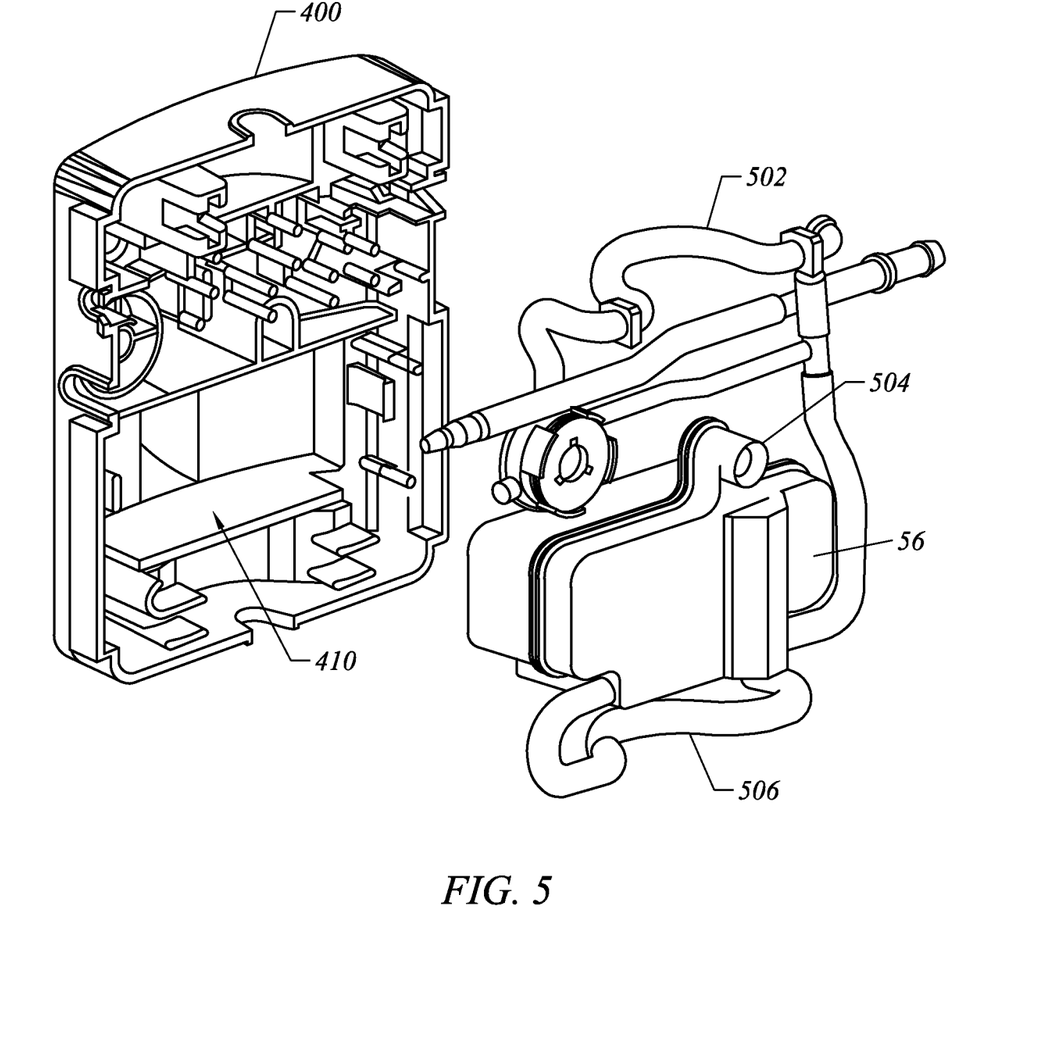
FIG. 5 is a perspective view showing a dual mode fluid network that is mountable on a common cassette frame.

In one embodiment of the present invention, fluid networks specialized for each different type of cassette (e.g., single mode or dual mode) can be interchangeably mounted within a common cassette frame. With reference to FIGS. 4 and 5, a single mode fluid network 402 (displacement mode only) and a dual mode fluid network 502 are both mountable on a common cassette frame 400. The common cassette frame 400 includes channels and receptacles for receiving and securing the fluid networks' tubing, valves, tanks, etc. The cassette frame and the fluid networks are cooperatively designed such that the cassette frame is capable of receiving multiple, differently configured fluid networks. By utilizing a common frame for multiple types of cassettes, the present invention may eliminate or reduce the excess production and inventory costs related to having multiple types of cassettes. The common frame 400 also makes it easier for the console to accept multiple types of cassettes, whereby at least the physical dimensions of the cassette frame remain the same amongst different types of cassettes.

As shown in FIG. 5, fluid network 502, which is a dual mode fluid network that enables vacuum-based aspiration, includes a holding tank 56 that is not present in fluid network 402. Tank 56 may be connected to a vacuum pump (e.g., a Venturi pump) located in the surgical console and may provide vacuum-based aspiration to the handpiece when selector valve 58 (FIG. 2) connects the handpiece to the vacuum generated in tank 56. As illustrated by FIG. 5, common cassette frame 400 may include a receptacle 410 configured to receive holding tank 56. The holding tank may also receive aspirated fluids before the fluid is drained to the collection bag.

Figure 5A:
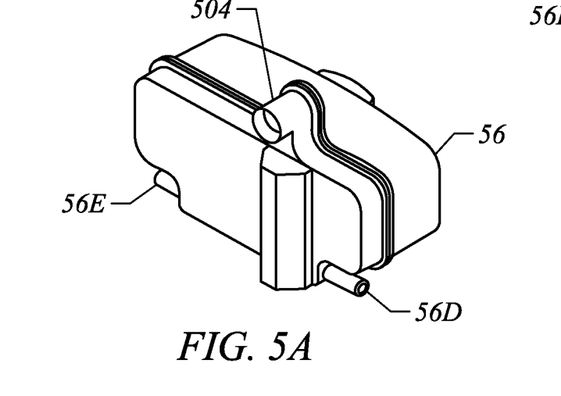
FIGS. 5A-C are perspective views of the holding tank of the dual mode fluid network of FIG. 5.
Figure 5B:
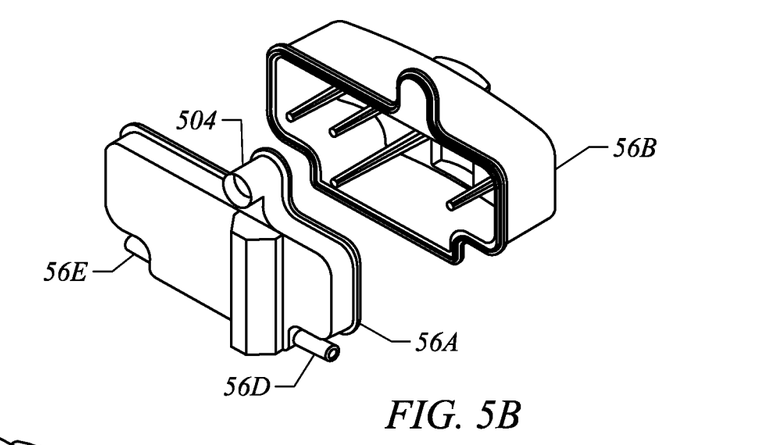
Figure 5C:
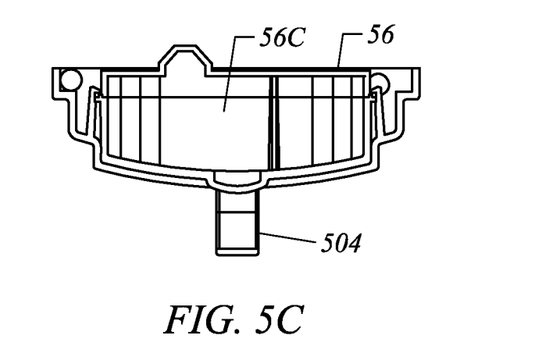

FIGS. 5A-C illustrate an exemplary holding tank 56 from dual mode fluid network 502. In particular, tank 56 may be formed from two clear plastic pieces 56A and 56B to define a hollow interior 56C therein. The tank may include a connecting stem 504 that communicates with hollow interior 56C and connects the tank to an exterior vacuum source (e.g., a vacuum pump located in the console). Tank 56 may also include connectors 56D and 56E, which allow the tank to be connected to the fluid network via tubing. For example, connector 56D may connect the holding tank (via the selector valve) to the handpiece 12 (FIG. 2). Vacuum suction may be provided to the handpiece through connector 56D and aspirated fluids may be received into the holding tank via this connector. Connector 56E may connect the holding tank to the collection bag 62 (FIG. 2). Tubing that leads from connector 56E to the collection bag may include an arcuate section 506 (FIG. 5) that enables displacement-based evacuation of the fluids in the holding tank when coupled with a peristaltic pump (e.g., pump 60 of FIG. 2). Accordingly, the holding tank 56 may be connected to the fluid network when vacuum-based aspiration is desired. When not needed, the separable holding tank 56 may be removed from the fluid network to reduce the cost of the cassette.

Figure 7:
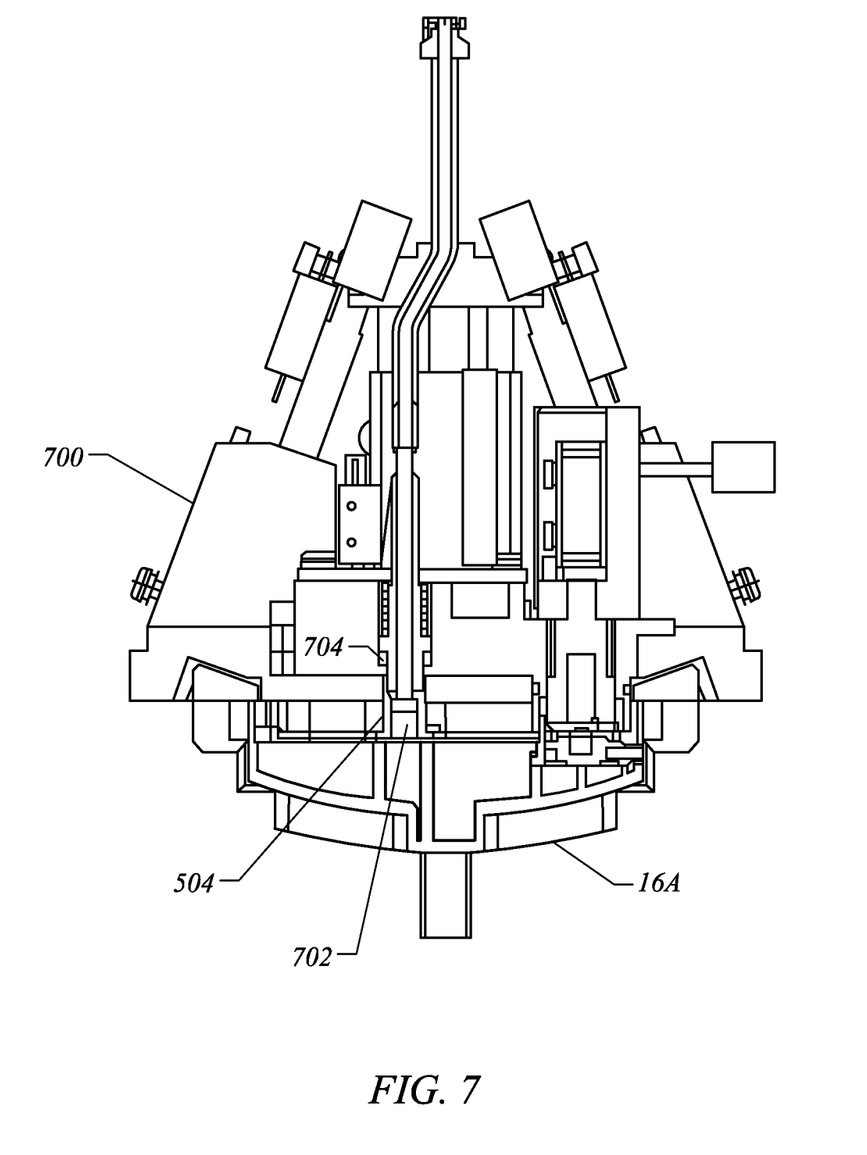
FIG. 7 is a plan view showing the actuation of a microswitch in the console by a functional indicator of the eye treatment cassette.

The console and the cassette may communicate to establish the functionality of the mounted cassette (i.e., the modes of aspiration enabled by the cassette). In one approach, a cassette may include a functional indicator that is detected by the console and which identifies the available functionalities of the installed cassette. For example, with reference to FIG. 5, fluid network 502 for a dual mode cassette includes the holding tank 56. Holding tank 56 includes a connecting stem 504, which connects the holding tank with a vacuum pump (not shown) located in the surgical console on which the dual mode cassette 16A is mounted. With reference to FIG. 7, engagement of the connecting stem 504 with a sealing nipple 702 of the surgical console 700 may actuate a microswitch 704 and indicate to the console that vacuum-enabled cassette 16A has been installed. In response, the console 700 may activate its vacuum pump and other necessary mechanism in preparation for vacuum-based aspiration. Thus, indigenous or native element of the dual mode cassette 16A, that is, the holding tank 56 with the connecting stem 504, are utilized to communicate to the console to establish a functionality of the mounted cassette.

Figure 7A:
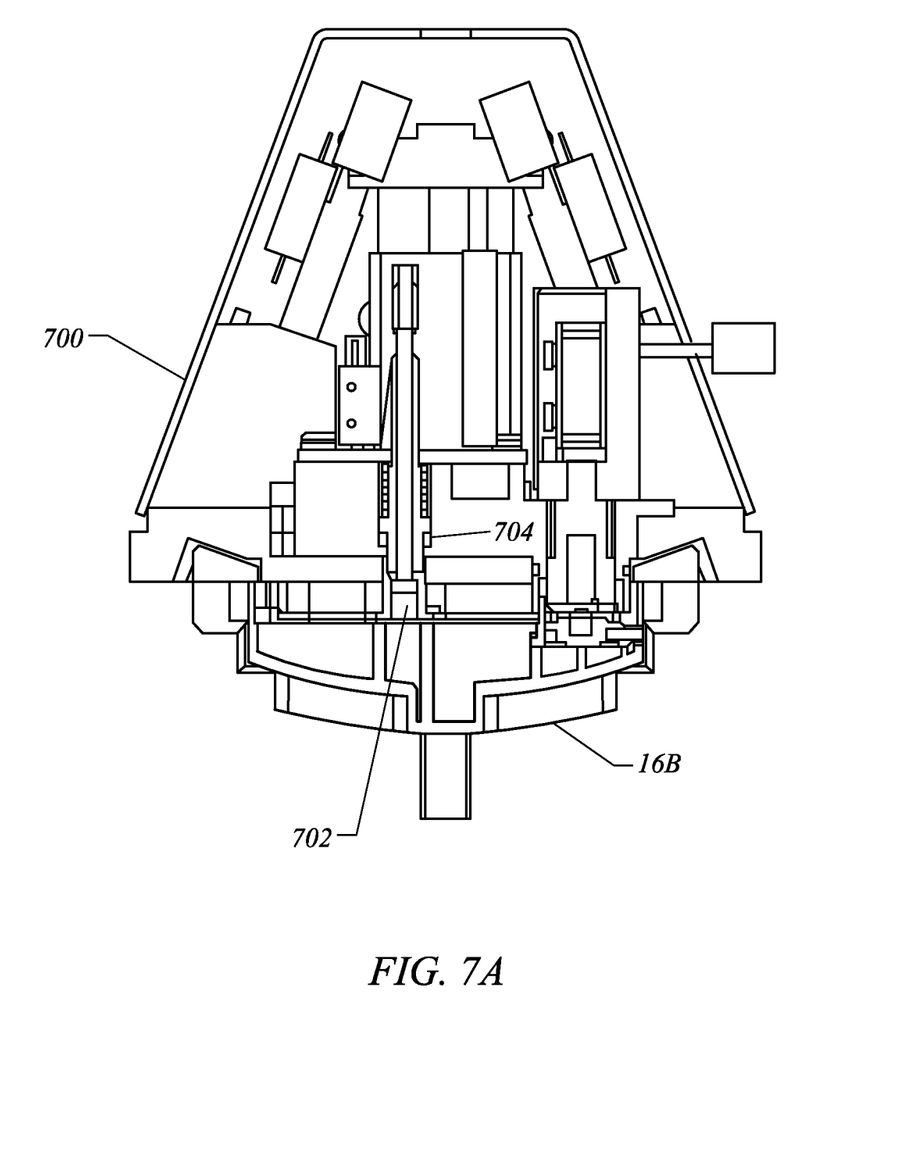
FIG. 7A is a plan view showing a position of the microswitch in the console when the installed eye treatment cassette does not have a functional indicator.

By contrast, as illustrated by FIG. 7A, the cassette 16B does not contain a holding tank 56 with a connecting stem 504, indigenous to the operation of cassette 16A within the system. Thus, when cassette 16B is installed on console 700, microswitch 704 is not triggered because no holding tank is native to the cassette 16B. Accordingly, the console will be informed that no vacuum-based aspiration is available with the mounted cassette. Therefore, utilizing a functional indicator (absence of a holding tank 56 with a connecting stem 504), the surgical console may be informed upon mounting of the cassette that vacuum-based aspiration is available with the mounted cassette. In an embodiment where only two different cassettes are available (i.e., a displacement mode cassette and a dual mode cassette with vacuum aspiration), the console may confirm by presence of the holding tank which of the two types of cassettes has been mounted on the console. In some embodiments the use of an indigenous element or function may increase the reliability of accurately communicating correct mode or functionality information, since the communication is based on an actual cassette capability and not on, for example, on a modification to the cassette frame or a component of the cassette which correlates with a function that may or may not actually be present. An example of the later might include the use of a tab that is left or removed from the cassette body, depending of capability of the cassette to support vacuum pump operation. In this case, for example due to a human error, the tab might be incorrectly set to communication support of vacuum pump operation, when in fact no such support exist.

It should be understood that the foregoing example of the use of an indigenous element of the cassette is illustrative only. Alternative methods and structures may also be used. For example, a non-mechanical method may be used where the cassette is labeled with a bar code containing functional information that is automatically scanned by the console. Regardless of the specific method used, the console and cassette of the present invention communicate to establish the functionalities available with the installed cassette, and the console prepares itself accordingly.

Figure 6:
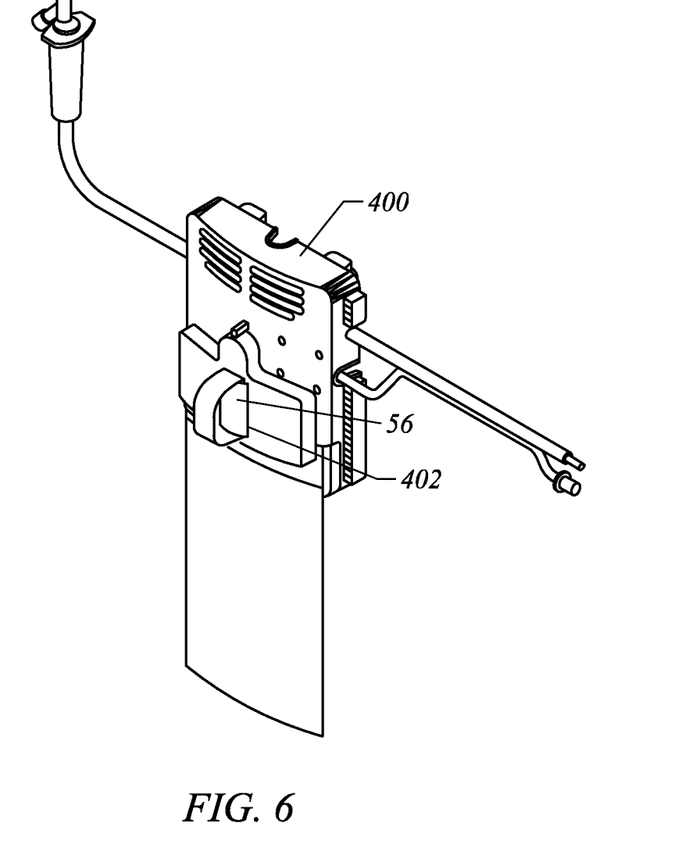
FIG. 6 is a perspective view showing an eye treatment cassette having a visual indication of its functionality.

The exemplary cassette may possess a visual indicator of its functionality (i.e., the aspiration modes enabled by the cassette). For example, with reference to FIG. 6, cassette frame 400 may include a window 404 through which the holding tank 56 of a dual mode fluid network may be seen. Therefore, if a holding tank is visible through window 402, a system operator will be informed that vacuum-based aspiration is available with the mounted cassette. In an embodiment where only two different cassettes are available (i.e., a displacement mode cassette and a dual mode cassette with vacuum aspiration), an operator may also visually confirm which of the two types of cassettes has been mounted on the console. Other visual indicia, such as alphanumeric codes or color-coded patches, may also be used to indicate the functionality of the cassette. In some embodiments, a clear cassette may be provided through which the presence of a holding tank may be visually confirmed and indicate the functionality of the cassette.

Figure 8:
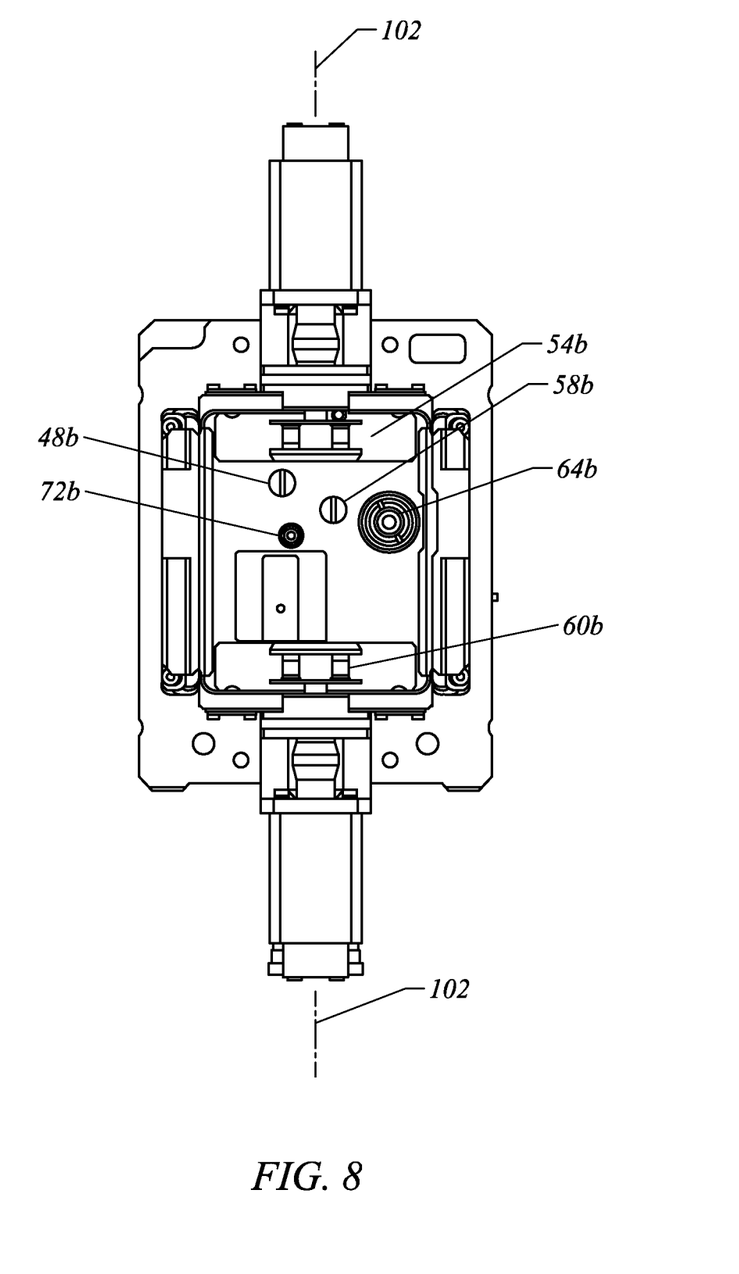
FIG. 8 is a plan view showing the coupling components of a console configured to receive multiple types of eye treatment cassettes.

FIG. 8 illustrates a surgical console of the present invention which interchangeably receives multiple types of fluidic cassettes that enable one or both of displacement-based and vacuum-based aspiration modes. Engagement between the cassette and the cassette receptacle of console 14 can be understood with reference to FIGS. 2, 3, and 8. In particular, aspiration drive rotor 54b rotates about axis 102 and drives peristaltic pump 54 in either cassette 16A or 16B. Pressure receiver 64b and valve actuator 48b respectively couple with vacuum sensor 64 and irrigation valve 48 mounted in either type of cassette. When dual mode cassette 16A is mounted on the console, drain drive rotor 60 rotates about axis 102 to drive peristaltic drain pump 60 in the cassette. Valve actuator 58b is coupled with switching valve 58 of cassette 16A. Vacuum coupler 72b couples with holding tank 56 of cassette 16A. And, as previously described with respect to FIGS. 5 and 7, connecting stem 504 of holding tank 56 actuates a microswitch 704 within coupler 72b and indicates to the console that vacuum aspiration is available with the mounted cassette. It should be understood that the console may use other methods to actively detect or passively receive information from the mounted cassette regarding its functionality.

While the exemplary embodiments have been described in some detail for clarity of understanding and by way of example, a variety of changes, modifications, and adaptations will be obvious to those of skill in the art. Hence, the scope of the present invention is limited solely by the appended claims.

What is claimed is:

1. An eye treatment cassette for use with an eye treatment console, the eye treatment console comprising a receptacle, a peristaltic pump exposed to the receptacle to facilitate a positive displacement aspiration functionality, a vacuum source that is part of a vacuum-based system and coupleable to the receptacle to induce a vacuum-based aspiration functionality, and a cassette functional indicator detector, the eye treatment cassette comprising:
- a cassette frame;
- an aspiration pathway coupleable to at least one of the peristaltic pump or the vacuum source when the cassette frame is mounted in the receptacle; and
- a cassette functional indicator that signals a functionality of the eye treatment cassette to the detector of the console so as to allow the console to selectively drive at least one of the positive displacement aspiration with the peristaltic pump or vacuum-based aspiration with the vacuum-based system based on the functionality of the eye treatment cassette.

2. The eye treatment cassette of claim 1, further comprising a vacuum sensor for sensing a pressure in the aspiration pathway.

3. The eye treatment cassette of claim 1, further comprising an output connecting the aspiration pathway with a collection bag.

4. The eye treatment cassette of claim 1, further comprising an irrigation pathway for receiving an irrigation flow.

5. The eye treatment cassette of claim 1, wherein the vacuum source is a Venturi pump.

6. The eye treatment cassette of claim 1, wherein the vacuum source is a rotary vane pump.

* * * * *